United States Patent
Govari et al.

(10) Patent No.: US 10,405,776 B2
(45) Date of Patent: Sep. 10, 2019

(54) POSITIONING TOOL FOR AN ORTHOPEDIC IMPLANT

(71) Applicant: Biosense Webster (Israel) Ltd., Yokneam (IL)

(72) Inventors: Assaf Govari, Haifa (IL); Andres Claudio Altmann, Haifa (IL); Vadim Gliner, Haifa (IL); Yehuda Algawi, Binyamina (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 288 days.

(21) Appl. No.: 15/621,677

(22) Filed: Jun. 13, 2017

(65) Prior Publication Data
US 2018/0353102 A1    Dec. 13, 2018

(51) Int. Cl.
*A61B 5/06* (2006.01)
*A61B 17/17* (2006.01)
*A61B 90/00* (2016.01)
*A61B 34/20* (2016.01)

(52) U.S. Cl.
CPC .......... *A61B 5/062* (2013.01); *A61B 17/1703* (2013.01); *A61B 17/1717* (2013.01); *A61B 34/20* (2016.02); *A61B 90/37* (2016.02); *A61B 90/39* (2016.02); *A61B 17/1707* (2013.01); *A61B 17/1725* (2013.01); *A61B 2034/2051* (2016.02); *A61B 2090/3958* (2016.02)

(58) Field of Classification Search
CPC ................................ A61B 5/062; A61B 34/20
See application file for complete search history.

(56) References Cited

U.S. PATENT DOCUMENTS

| | | | | |
|---|---|---|---|---|
| 5,105,829 | A | * 4/1992 | Fabian | A61B 5/06 128/899 |
| 5,391,199 | A | 2/1995 | Ben Haim | |
| 5,584,838 | A | 12/1996 | Rona | |
| 5,711,299 | A | * 1/1998 | Manwaring | A61B 5/06 128/899 |
| 6,239,724 | B1 | 5/2001 | Doron | |

(Continued)

FOREIGN PATENT DOCUMENTS

| | | |
|---|---|---|
| EP | 3363359 A1 | 8/2018 |
| WO | WO 96-05768 A1 | 2/1996 |

OTHER PUBLICATIONS

Extended European Search Report for corresponding European patent application No. 18177191.6, dated Nov. 2, 2018.

*Primary Examiner* — Christian A Sevilla
(74) *Attorney, Agent, or Firm* — Notaro, Michalos & Zaccaria P.C.

(57) ABSTRACT

An apparatus for positioning an orthopedic implant, the apparatus includes a flexible substrate, at least first and second field-generating coils, and circuitry. The flexible substrate is formed into a three-dimensional (3D) shape and is coupled to a predefined location on the orthopedic implant. The at least first and second field-generating coils are formed in the flexible substrate, such that in the 3D shape the first and second field-generating coils have first and second respective axes that are not parallel to one another. The circuitry is mounted on the flexible substrate and electrically connected to the at least first and second field-generating coils, and is configured to drive the at least first and second field-generating coils with respective signals.

22 Claims, 2 Drawing Sheets

(56) References Cited

U.S. PATENT DOCUMENTS

| | | |
|---|---|---|
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben Haim |
| 7,003,342 B2 * | 2/2006 | Plaza .................. A61B 5/0422 600/374 |
| 7,658,196 B2 * | 2/2010 | Ferreri .................... A61B 5/06 128/899 |
| 8,203,343 B1 | 6/2012 | Olsson |
| 8,755,888 B2 * | 6/2014 | Voznesensky ..... A61N 1/36007 607/40 |
| 2002/0065455 A1 | 5/2002 | Ben Haim |
| 2003/0120150 A1 | 6/2003 | Govari |
| 2003/0187347 A1 | 10/2003 | Nevo et al. |
| 2004/0034355 A1 | 2/2004 | Govari |
| 2004/0059212 A1 | 3/2004 | Abreu |
| 2004/0068178 A1 | 4/2004 | Govari |
| 2005/0070916 A1 | 3/2005 | Hollstien et al. |
| 2008/0086145 A1 | 4/2008 | Sherman |
| 2013/0066194 A1 | 3/2013 | Seter |

\* cited by examiner

POSITIONING TOOL FOR AN ORTHOPEDIC IMPLANT

FIELD OF THE INVENTION

The present invention relates generally to medical devices, and particularly to methods and systems for positioning an orthopedic implant within a patient body.

BACKGROUND OF THE INVENTION

Orthopedic implants, such as intramedullary nails, are implanted in bone tissue of a patient. Various methods and systems are known in the art for tracking the position of an orthopedic implant inside the patient body.

For example, U.S. Patent Application Publication 2004/0034355 describes method and apparatus for distal targeting of locking screws in intramedullary nails. A sensor, such as a wireless sensor, having a plurality of field transponders, is disposed in an orthopedic appliance, such as an intramedullary nail. The sensor is capable of detecting and discriminating the strength and direction of the different fields generated by the field generators.

U.S. Patent Application Publication 2008/0086145 describes a system that enables targeting of an instrument placed within a drill bushing aligns the axis of a drill bushing with the axis of a transverse hole in an intramedullary nail. The system includes a probe having an elongated member with a distal end, a magnet that is polarized along its longitudinal axis that is mounted perpendicularly to the distal end of the elongated member; and a processor executing programmed instructions to determine a position and orientation of the magnetic sensor array with respect to the targeting magnet.

U.S. Pat. No. 5,584,838 describes a femoral nail which has a transverse hole, and an arrangement for generating a magnetic field which has a maximum strength along an axis of the transverse hole and which decreases in strength in directions radially away from the axis.

SUMMARY OF THE INVENTION

An embodiment of the present invention that is described herein provides an apparatus for positioning an orthopedic implant, the apparatus includes a flexible substrate, at least first and second field-generating coils, and circuitry. The flexible substrate is formed into a three-dimensional (3D) shape and is coupled to a predefined location on the orthopedic implant. The at least first and second field-generating coils are formed in the flexible substrate, such that in the 3D shape the first and second field-generating coils have first and second respective axes that are not parallel to one another. The circuitry is mounted on the flexible substrate and electrically connected to the at least first and second field-generating coils, and is configured to drive the at least first and second field-generating coils with respective signals.

In some embodiments, the flexible substrate includes a flexible circuit board. In other embodiments, the at least first and second field-generating coils are formed in a single layer of the flexible substrate. In yet other embodiments, the at least first and second field-generating coils are formed in first and second respective layers of the flexible substrate.

In an embodiment, the apparatus includes a third field-generating coil, in the 3D shape, the third field-generating coil has a third axis that is not parallel to any of the first and second axes. In another embodiment, the apparatus includes one or more sensors, which are configured to sense respective components of one or more magnetic fields generated by the at least first and second field-generating coils, and to produce corresponding electrical signals indicative of the sensed components of the one or more magnetic fields. In yet another embodiment, the apparatus further includes a processor, which is electrically connected to the one or more sensors, and is configured to display, based on the electrical signals, a position of the orthopedic implant within a body of a patient.

In some embodiments, the one or more sensors include one or more magnetic receivers, coupled to an external unit. In other embodiments, the orthopedic implant includes an opening, and the at least first and second field-generating coils are set at respective first and second offsets relative to the opening. In yet other embodiments, in the 3D shape, the first and second axes are orthogonal to one another.

In an embodiment, the circuitry includes a power source, which is configured to supply electrical power to the circuitry. In another embodiment, the power source includes a battery, or circuitry, which is configured to harvest electrical power from energy transmitted by an external unit. In yet another embodiment, the external unit includes an industrial, scientific and medical (ISM) radiator, which is configured to transmit ISM electromagnetic energy, and the circuitry is configured to harvest electrical power from the ISM electromagnetic energy.

In some embodiments, the apparatus includes an inert biocompatible sleeve, which is configured to seal the flexible substrate from interacting with tissue of an implantee of the orthopedic implant. In other embodiments, the flexible substrate is configured to be coupled to any arbitrary-shaped three-dimensional (3D) implant.

There is additionally provided, in accordance with an embodiment of the present invention, a method for producing an orthopedic implant, the method including providing a flexible substrate, which is formed into a three-dimensional (3D) shape. Tt least first and second field-generating coils, are formed in the flexible substrate, such that in the 3D shape the first and second field-generating coils have first and second respective axes that are not parallel to one another. Circuitry for driving the at least first and second field-generating coils, is mounted on the flexible substrate, and the circuitry is electrically connected to the at least first and second field-generating coils. The flexible substrate is coupled to a predefined location on the orthopedic implant.

There is further provided, in accordance with an embodiment of the present invention, a method for positioning an orthopedic implant, the method including inserting into a receiving bone the orthopedic implant that includes a flexible substrate, which is formed into a three-dimensional (3D) shape and is coupled to a predefined location on the orthopedic implant, at least first and second field-generating coils formed in the flexible substrate, such that in the 3D shape the first and second field-generating coils have first and second respective axes that are not parallel to one another, and circuitry, which is mounted on the flexible substrate and electrically connected to the at least first and second field-generating coils, and which is configured to drive the at least first and second field-generating coils with respective signals. The orthopedic implant is navigated to a target location within the receiving bone, and a position of the orthopedic implant is tracked by sensing electromagnetic fields produced by the at least first and second field-generating coils.

The present invention will be more fully understood from the following detailed description of the embodiments thereof, taken together with the drawings in which:

DETAILED DESCRIPTION OF EMBODIMENTS

Overview

Figure 1:
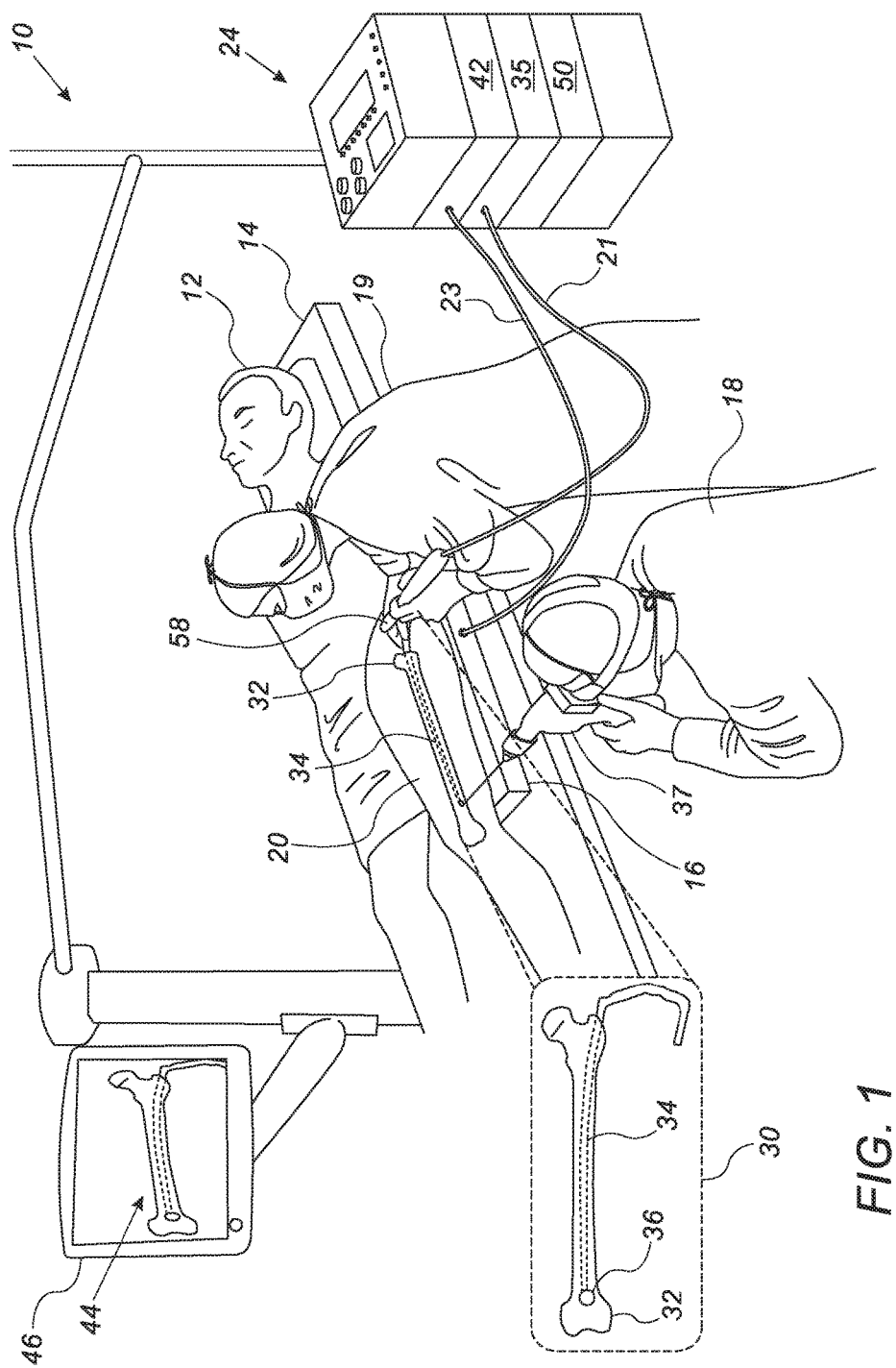
FIG. 1 is a schematic, pictorial illustration of an orthopedic procedure applying a system for implanting an orthopedic implant in a patient bone, in accordance with an embodiment of the present invention.

Orthopedic implants, such as an intramedullary nail, are typically fixed to a receiving bone by drilling one or more holes into the bone, and fitting fixing apparatus, such as orthopedic screws, through the drilled holes and designated openings in the nail. A physician may apply anatomical imaging techniques, such as fluoroscopy, to align the designated openings with the drilled holes. However, it is highly desirable to reduce the amount of radiation in such procedures.

Embodiments of the present invention that are described hereinbelow provide improved techniques for aligning a designated opening in an orthopedic implant with a hole drilled by the physician in the bone. In some embodiments, the physician applies a positioning apparatus for aligning the position and orientation of the opening with the drilled hole.

In some embodiments, the positioning apparatus comprises a field-generator that is coupled to a predefined location on the orthopedic implant, e.g., at a predefined offset relative to the opening. The field-generator comprises a flexible substrate, which is configured to be formed (e.g., rolled) into a given three-dimensional (3D) shape, such as a cylindrical shape.

In some embodiments, the positioning apparatus comprises three field-generating coils electrically isolated from one another. The coils are formed in the flexible substrate, such that when formed into the 3D shape the coils have respective three axes that are orthogonal to one another. The coils may be formed on a single layer, or on multiple, e.g., three, layers of the flexible substrate, and are configured to generate a triple-axis magnetic field in the directions of the respective axes.

In some embodiments, the apparatus comprises circuitry, which is mounted on the flexible substrate and is electrically connected to each of the field-generating coils. The circuitry is configured to harvest electrical power from electromagnetic (EM) energy, transmitted by an external unit, e.g., a wireless wand, and to drive the field-generating coils with respective alternating current (AC) signals, using the EM energy.

In some embodiments, the external unit further comprises a magnetic receiver that comprises one or more magnetic position sensors, which are configured to sense components of the triple-axis magnetic field and to transmit, to a processor, respective signals indicative of the position of the field-generator within the receiving bone. In other embodiments, the magnetic receiver may be located separately from the external unit, e.g., below the patient thigh. In an embodiment, the processor is configured to receive the signals and to display the position and orientation of the opening, overlaid on a pre-acquired anatomical image of the patient thigh, so as to assist the physician to align the opening of the implant with the hole drilled in the receiving bone.

The disclosed techniques enable fixing an implant to a receiving bone without exposing the patient and physician to hazardous X-ray radiation. These techniques enable reducing the cost and complexity of orthopedic implants, shortening the cycle time of orthopedic implanting procedures, and improving the safety of the patient and physician.

System Description

FIG. 1 is a schematic, pictorial illustration of an orthopedic procedure using system 10 for implanting an orthopedic implant 34 in a thigh 20 of a patient 12, in accordance with an embodiment of the present invention. In the example of FIG. 1, physicians 18 and 19 are implanting orthopedic implant 34 in a receiving bone 32 (e.g., a thigh bone) of patient 12 lying on an operating table 14. In the present context, the terms "patient" and "implantee" are used interchangeably, and refer to a recipient of implant 34.

In some embodiments, system 10 comprises a magnetic position tracking system comprising field-generators (shown in FIG. 2), a magnetic receiver 16 located below thigh 20 and/or within a wand 58, and additional components that will be described in detail below.

In some embodiments, wand 58 further comprises an industrial, scientific and medical (ISM) radiator, depicted in detail in FIG. 2 below.

In some embodiments, system 10 comprises an operating console 24, which comprises a processor 42, typically a general-purpose computer, with suitable front end and interface circuits for receiving signals from multiple sources of system 10, and for controlling the other components of system 20 described herein.

In some embodiments, magnetic receiver 16 comprises one or more magnetic position sensors, configured to sense magnetic fields, and connected to the interface circuitry in processor 42 via a cable 23. Processor 42 may be programmed in software to carry out the functions that are used by the system, and the processor stores data for the software in a memory 50. The software may be downloaded to console 24 in electronic form, over a network, for example, or it may be provided on non-transitory tangible media, such as optical, magnetic or electronic memory media. Alternatively, some or all of the functions of processor 42 may be carried out by dedicated or programmable digital hardware components.

In some embodiments, physician 18 drills a hole through the skin, flesh and bone 32 of thigh 20, using a drilling tool 37, or any other suitable technique.

Reference is now made to an inset 30 showing implant 24 positioned within bone 32. In the exemplary procedure depicted in FIG. 1, physician 19 navigates implant 34 to a target position within bone 32, in which the drilled hole in bone 32 is aligned with a designated opening 36 of implant 34. Subsequently, physician 18 fixes implant 34 to bone 32 by fitting a fixing apparatus (not shown), such as an orthopedic screw, into the aligned hole of bone 32 and opening 36 of implant 34.

In some embodiments, console 24 comprises a driver circuit 35 that is configured to drive, via a cable 21, the ISM radiator of wand 58, operated by physician 19 or by any other operator. The ISM radiator and field-generator (shown in FIG. 2) are described in detail in FIG. 2 below.

In some embodiments, processor 42 is configured to display, on a user display 46, the position and orientation of orthopedic implant 34 overlaid (e.g., as a marker) on a pre-acquired anatomical image 44 of bone 32.

This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Figure 2:
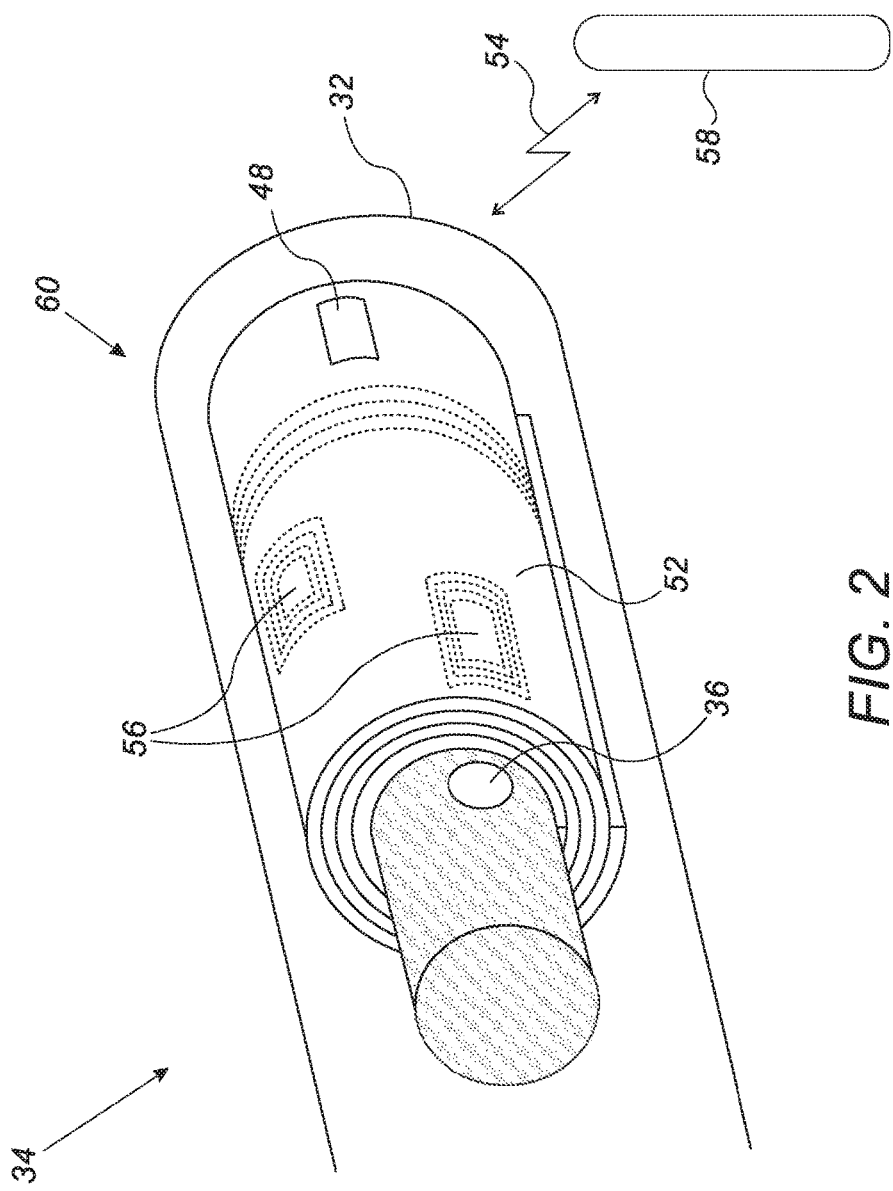
FIG. 2 is a schematic, pictorial illustration of a field-generator used for tracking and positioning an orthopedic implant in a patient bone, in accordance with an embodiment of the present invention.

Navigating an Orthopedic Implant in a Receiving Bone using a Wireless Positioning Tool FIG. 2 is a schematic, pictorial illustration of a field-generator 60 used for setting the position and orientation of orthopedic implant 34 in bone 32, in accordance with an embodiment of the present invention.

In some embodiments, field-generator 60 comprises a flexible substrate, rolled around implant 34 at a predefined location relative to opening 36.

In some embodiments, the flexible substrate comprises a flexible circuit board 52 made from Kapton™ or any other suitable material. In some embodiments, one or more coils (typically three), such as coils 56, are formed on a single layer, or within multiple (e.g., three) respective layers of board 52. Coils 56 are made from a conductive material, such as copper, and are formed on board 52 using any suitable production technique.

In this configuration, each coil 56 has an axis orthogonal to the surface of board 52. In some embodiments, the axes of coils 56 are typically orthogonal to one another, but can be oriented relative to one another at any other suitable angle different from zero. In other words, the axes of coils 56 are not parallel to one another.

In some embodiments, three coils 56 of field-generator 60, are configured to apply to bone 32 a triple-axis magnetic field in the directions of the respective axes. The magnetic field is detected by the magnetic position sensors of receiver 16 and signals indicative of the position of field-generator 60 are transmitted to processor 42 via cable 23.

In alternative embodiments, the magnetic field is detected by the magnetic receiver of wand 58, and signals indicative of the position of field-generator 60 are transmitted to processor 42 via cable 21 and circuitry 35.

In these embodiments, the magnetic receiver of wand 58 may replace magnetic receiver 16, and circuitry 35 may further comprise a processor (not shown) that may replace processor 42.

In some embodiments, circuitry 48, which is mounted on board 52, is configured to harvest electrical power from electromagnetic (EM) energy 54 transmitted by the ISM radiator of wand 58. In some embodiments, the EM energy comprises an unlicensed ISM band power frequency, such as 13.56 MHz.

In some embodiments, circuitry 48 comprises a signal-generator, which is configured to generate three different alternate current (AC) signals at three different respective frequencies. Circuitry 48 is electrically connected to coils 56 so that each AC signal is used for driving a respective coil 56.

In some embodiments, circuitry 48 comprises a power source configured to supply electrical power to the signal-generator for driving coils 56.

In some embodiments the power source my apply energy harvesting techniques. For example, a device comprising one or more piezoelectric elements may be applied for harvesting energy from ambient temperature, vibration or flow of fluids within thigh 20. In an embodiment, the one or more piezoelectric elements may be activated by an external source that is configured to generate vibrations or to transfer acoustic pulses to the piezoelectric elements.

In alternative embodiments, circuitry 48 may comprise an implantable battery, which is configured to supply power to the signal-generator.

In some embodiments, field-generator 60 is sealed from tissue (e.g., bone 32) of patient 12, using an inert biocompatible sleeve made from Teflon™ or by using any other suitable sealing technique.

In some embodiments, physician 19 inserts implant 34, having field-generator 60 coupled thereto, into bone 32 and holds wand 58 in close proximity to circuitry 48 so as to transmit energy 54 thereto. Circuitry 48 converts energy 54 to AC signals driving coils 56, which produce the triple-axis magnetic field. In an embodiment, the magnetic receiver of wand 58 (and/or magnetic receiver 16) senses the magnetic field applied by coils 56, and transmits signals indicative of the position and orientation of field-generator 60 to processor 42.

In an embodiment, processor 42 estimates the position and orientation of opening 36 within bone 32 using the received signals indicating the position of field-generator 60 and respective predefined offset of each coil 56 relative to opening 36. In this embodiment, processor 42 tracks the position and orientation of opening 36 and displays a marker indicative of the position and orientation of opening 36 overlaid on image 44 of bone 32.

In an embodiment, based on the position and orientation of the marker, physician 19 navigates implant 34 within bone 32 to a target position, in which the drilled hole of bone 32 is aligned with opening 36 of implant 34. Subsequently, fixes implant 34 to bone 32 by fitting the fixing apparatus into the hole of bone 32 and opening 36 of implant 34.

In alternative embodiments, field-generator 60 may comprise any suitable number of coils, having any suitable shape and arranged so that board 52 may be folded into any suitable shape, thereby arranging the axes of coils 56 at any suitable angle, which is typically not parallel with one another.

In these embodiments, the signal-generator of circuitry 48 is configured to generate any suitable number of AC signals for driving a respective number of coils. Furthermore, the flexibility of board 52 enables coupling field-generator 60 to any arbitrary-shaped three-dimensional (3D) implant, not limited to any specific shape.

In some embodiments, implant 34 refers to any type of orthopedic implant, such as a nail, a pin, a plate and a prosthesis, implanted in a limb or spine or any other bone tissue of patient 12.

The specific configurations shown in FIGS. 1 and 2 are simplified for the sake of clarity and are depicted purely by way of example. In alternative embodiments, system 10 may comprise any other suitable positioning and or position tracking apparatus, and those having ordinary skill in the art will be able to adapt the description, mutatis mutandis, for other types of medical systems. Furthermore, the configuration of field-generator 60 is depicted purely by way of example, any other suitable configuration may be applied for producing the fields described above.

In alternative embodiments, system 10 may comprise a positioning tool configured to apply one or more magnetic fields externally to the patient body, and to sense the applied magnetic fields using one or more sensors coupled to implant 34. For example, magnetic receiver 16 is replaced with a location pad, comprising field-generators, which is configured to generate a triple-axis magnetic field. In these embodiments, circuit board 52 and coils 56 may be applied as a triple-axis sensor, configured to sense the applied triple-axis magnetic field.

In an embodiment, the triple-axis sensor is further configured to transmit electrical signals indicative of the position of implant 34, to processor 42. The electrical signals may be transmitted wirelessly, using any suitable technique, such as radio-frequency (RF), or Bluetooth low energy (BLE).

Although the embodiments described herein mainly address orthopedic implants, the methods and systems described herein can also be used in other applications, such as in a breast implant expender having an implantable port, a gastric band port, and an implantable reservoir of an insulin pump.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus for positioning an orthopedic implant, the apparatus comprising:
    a flexible substrate, which is formed into a three-dimensional (3D) shape and is coupled to a predefined location on the orthopedic implant;
    at least first and second field-generating coils formed in the flexible substrate, such that in the 3D shape the first and second field-generating coils have first and second respective axes that are not parallel to one another; and
    circuitry, which is mounted on the flexible substrate and electrically connected to the at least first and second field-generating coils, and which is configured to drive the at least first and second field-generating coils with respective signals.

2. The apparatus according to claim 1, wherein the flexible substrate comprises a flexible circuit board.

3. The apparatus according to claim 1, wherein the at least first and second field-generating coils are formed in a single layer of the flexible substrate.

4. The apparatus according to claim 1, wherein the at least first and second field-generating coils are formed in first and second respective layers of the flexible substrate.

5. The apparatus according to claim 1, and comprising a third field-generating coil, wherein, in the 3D shape, the third field-generating coil has a third axis that is not parallel to any of the first and second axes.

6. The apparatus according to claim 1, and comprising one or more sensors, which are configured to sense respective components of one or more magnetic fields generated by the at least first and second field-generating coils, and to produce corresponding electrical signals indicative of the sensed components of the one or more magnetic fields.

7. The apparatus according to claim 6, and comprising a processor, which is electrically connected to the one or more sensors, and is configured to display, based on the electrical signals, a position of the orthopedic implant within a body of a patient.

8. The apparatus according to claim 6, wherein the one or more sensors comprise one or more magnetic receivers, coupled to an external unit.

9. The apparatus according to claim 1, wherein the orthopedic implant comprises an opening, and wherein the at least first and second field-generating coils are set at respective first and second offsets relative to the opening.

10. The apparatus according to claim 1, wherein, in the 3D shape, the first and second axes are orthogonal to one another.

11. The apparatus according to claim 1, wherein the circuitry comprises a power source, which is configured to supply electrical power to the circuitry.

12. The apparatus according to claim 11, wherein the power source comprises a battery, or circuitry, which is configured to harvest electrical power from energy transmitted by an external unit.

13. The apparatus according to claim 12, wherein the external unit comprises an industrial, scientific and medical (ISM) radiator, which is configured to transmit ISM electromagnetic energy, and wherein the circuitry is configured to harvest electrical power from the ISM electromagnetic energy.

14. The apparatus according to claim 1, and comprising an inert biocompatible sleeve, which is configured to seal the flexible substrate from interacting with tissue of an implantee of the orthopedic implant.

15. The apparatus according to claim 1, wherein the flexible substrate is configured to be coupled to any arbitrary-shaped three-dimensional (3D) implant.

16. A method for producing an orthopedic implant, the method comprising:
    providing a flexible substrate, which is formed into a three-dimensional (3D) shape;
    forming in the flexible substrate, at least first and second field-generating coils, such that in the 3D shape the first and second field-generating coils have first and second respective axes that are not parallel to one another;
    mounting on the flexible substrate circuitry for driving the at least first and second field-generating coils, and electrically connecting the circuitry to the at least first and second field-generating coils; and
    coupling the flexible substrate to a predefined location on the orthopedic implant.

17. The method according to claim 16, wherein the orthopedic implant comprises an opening, and wherein coupling the flexible substrate comprises setting the at least first and second field-generating coils at respective first and second offsets relative to the opening.

18. The method according to claim 16, wherein forming the field-generating coils comprises forming the at least first and second field-generating coils in a single layer of the flexible substrate.

19. The method according to claim 16, wherein forming the field-generating coils comprises forming the at least first and second field-generating coils in first and second respective layers of the flexible substrate.

20. The method according to claim 16, wherein mounting the circuitry comprises mounting on the flexible substrate a power source for supplying electrical power to the circuitry.

21. A method for positioning an orthopedic implant, the method comprising:
- inserting into a receiving bone the orthopedic implant comprising:
  - a flexible substrate, which is formed into a three-dimensional (3D) shape and is coupled to a pre-defined location on the orthopedic implant;
  - at least first and second field-generating coils formed in the flexible substrate, such that in the 3D shape the first and second field-generating coils have first and second respective axes that are not parallel to one another; and
  - circuitry, which is mounted on the flexible substrate and electrically connected to the at least first and second field-generating coils, and which is configured to drive the at least first and second field-generating coils with respective signals; and
- navigating the orthopedic implant to a target location within the receiving bone, and tracking a position of the orthopedic implant by sensing electromagnetic fields produced by the at least first and second field-generating coils.

22. The method according to claim 21, wherein the orthopedic implant comprises an opening, and wherein navigating the orthopedic implant comprises aligning the opening with a hole formed in the receiving bone, and fitting a fixing apparatus into the aligned opening and hole.

* * * * *